(12) United States Patent
Farnan

(10) Patent No.: US 7,722,636 B2
(45) Date of Patent: May 25, 2010

(54) EMBOLIC DEVICE DELIVERY SYSTEM WITH TORQUE FRACTURE CHARACTERISTIC

(75) Inventor: Robert C. Farnan, Davie, FL (US)

(73) Assignee: Codman & Shurtleff, Inc., Raynham, MA (US)

( * ) Notice: Subject to any disclaimer, the term of this patent is extended or adjusted under 35 U.S.C. 154(b) by 394 days.

(21) Appl. No.: 11/290,965

(22) Filed: Nov. 30, 2005

(65) Prior Publication Data

US 2007/0123928 A1  May 31, 2007

(51) Int. Cl.
*A61M 29/00* (2006.01)
(52) U.S. Cl. .................................................. 606/200
(58) Field of Classification Search ............. 606/1, 606/191, 108, 200, 198
See application file for complete search history.

(56) References Cited

U.S. PATENT DOCUMENTS

| | | | |
|---|---|---|---|
| 3,963,322 A | 6/1976 | Gryctko | |
| 5,108,407 A | 4/1992 | Geremia et al. | |
| 5,117,838 A * | 6/1992 | Palmer et al. | 600/585 |
| 5,234,437 A | 8/1993 | Sepetka | |
| 5,261,916 A | 11/1993 | Engelson | |
| 5,263,964 A | 11/1993 | Purdy | |
| 5,427,118 A * | 6/1995 | Nita et al. | 600/585 |
| 5,725,546 A | 3/1998 | Samson | |
| 5,925,059 A | 7/1999 | Palermo et al. | |
| 5,989,242 A | 11/1999 | Saadat et al. | |
| RE37,117 E * | 3/2001 | Palermo | 606/1 |
| 6,217,566 B1 * | 4/2001 | Ju et al. | 604/526 |
| 6,296,622 B1 * | 10/2001 | Kurz et al. | 604/93.01 |
| 6,346,091 B1 * | 2/2002 | Jacobsen et al. | 604/57 |
| 6,451,026 B1 * | 9/2002 | Biagtan et al. | 606/108 |
| 6,478,773 B1 | 11/2002 | Gandhi et al. | |
| 6,638,293 B1 | 10/2003 | Makower et al. | |
| 6,685,653 B2 * | 2/2004 | Ehr et al. | 600/585 |
| 6,911,016 B2 * | 6/2005 | Balzum et al. | 604/95.04 |
| 7,323,000 B2 * | 1/2008 | Monstdt et al. | 606/200 |
| 2001/0044633 A1 | 11/2001 | Klint | |
| 2002/0022837 A1 | 2/2002 | Mazzocchi et al. | |
| 2002/0082499 A1 * | 6/2002 | Jacobsen et al. | 600/439 |
| 2003/0220666 A1 | 11/2003 | Mirigian | |
| 2004/0127918 A1 | 7/2004 | Nikolchev et al. | |
| 2005/0038470 A1 * | 2/2005 | van der Burg et al. | 606/213 |
| 2005/0113863 A1 * | 5/2005 | Ramzipoor et al. | 606/200 |
| 2006/0189896 A1 * | 8/2006 | Davis et al. | 600/585 |
| 2006/0200047 A1 * | 9/2006 | Galdonik et al. | 600/585 |
| 2007/0203519 A1 * | 8/2007 | Lorenzo et al. | 606/200 |
| 2007/0239191 A1 * | 10/2007 | Ramzipoor | 606/191 |
| 2007/0299422 A1 * | 12/2007 | Inganas et al. | 604/508 |

OTHER PUBLICATIONS

Partial European Search Report in EP 06 25 6125, dated Feb. 2, 2007.

* cited by examiner

*Primary Examiner*—Anhtuan T Nguyen
*Assistant Examiner*—Sarah A Simpson
(74) *Attorney, Agent, or Firm*—Cook Alex Ltd.

(57) ABSTRACT

A vascular occlusion device deployment system can deploy an occlusion device at a preselected site within the vasculature of a patient. The deployment system includes a pusher which employs an elongated member that releases an embolic device when a breakpoint of the elongated member is fractured by applying torque to the breakpoint such as by rotating the elongated member.

2 Claims, 2 Drawing Sheets

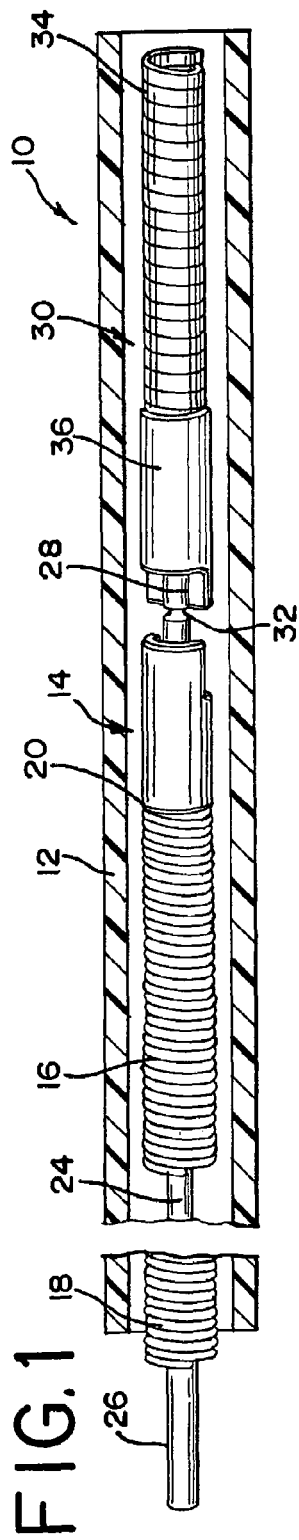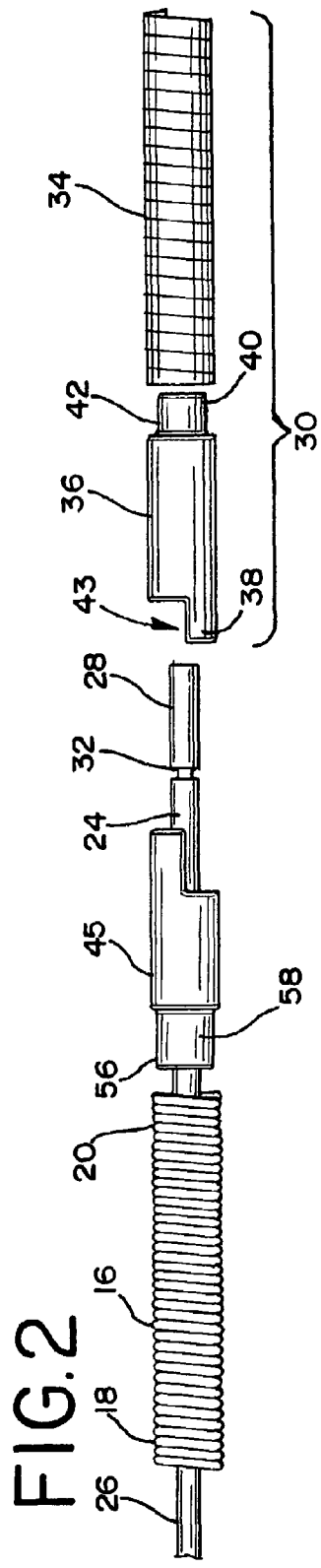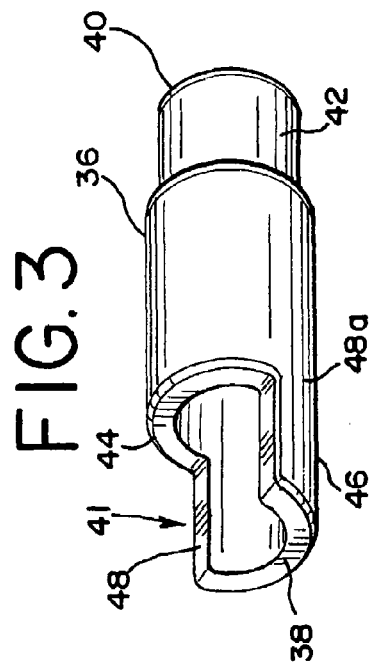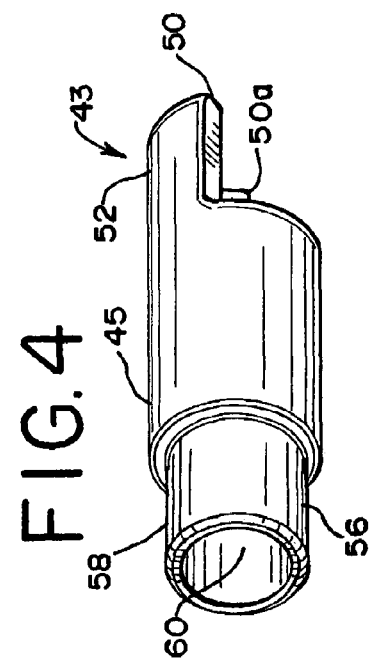

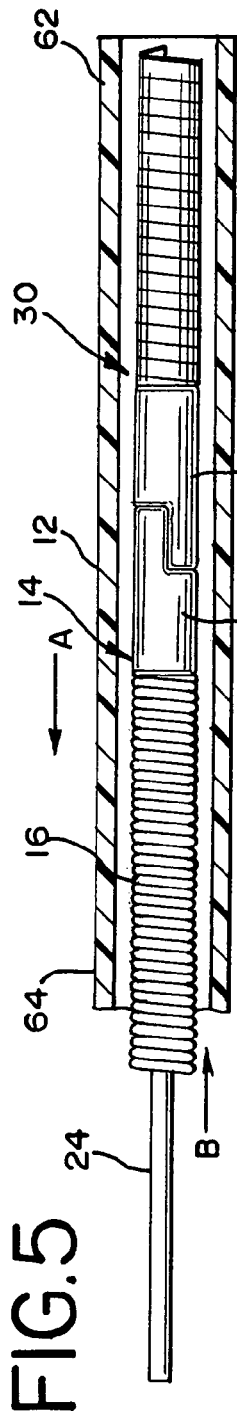
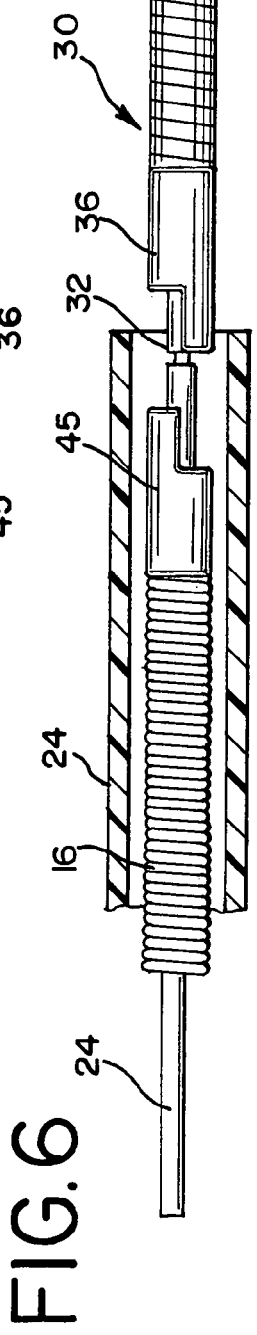
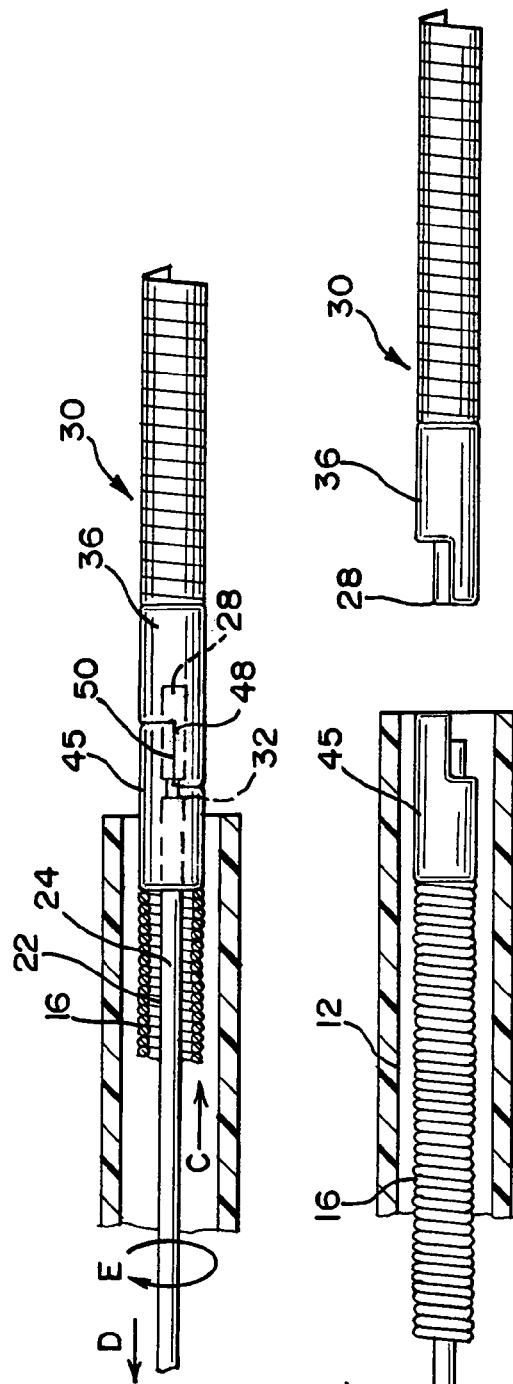
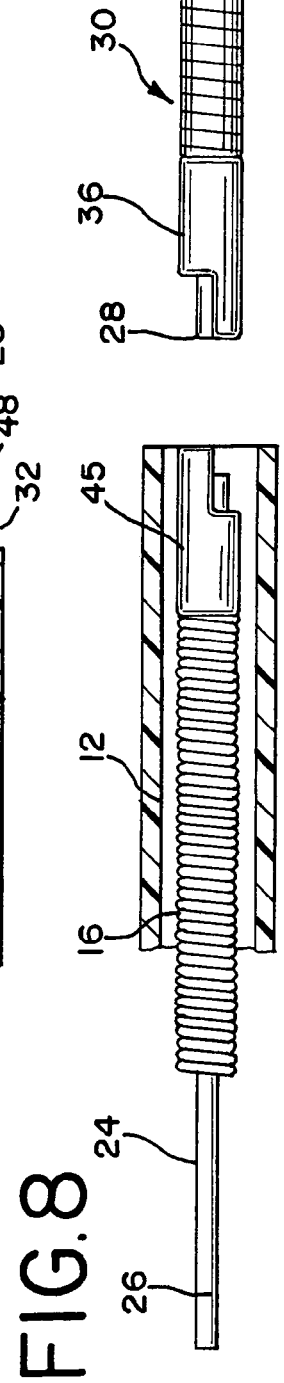
FIG. 5
FIG. 6
FIG. 7
FIG. 8

EMBOLIC DEVICE DELIVERY SYSTEM WITH TORQUE FRACTURE CHARACTERISTIC

FIELD OF THE INVENTION

The present invention is related to delivery of embolic occlusion devices. Disclosed are torque fracture deployment systems and methods for accurately and rapidly deploying occlusion devices at a preselected location within a patient. The deployment systems and methods are particularly suited for deploying an embolic coil at a location of concern within the vasculature of a patient.

BACKGROUND OF THE INVENTION

The use of catheter delivery systems for positioning and deploying therapeutic devices, such as dilation balloons, stents and embolic coils, in the vasculature of the human body has become a standard procedure for treating endovascular diseases. It has been found that such devices are particularly useful in treating areas where traditional operational procedures are impossible or pose a great risk to the patient, for example in the treatment of aneurysms in cranial blood vessels. Due to the delicate tissue surrounding cranial blood vessels, especially for example brain tissue, it is very difficult and often risky to perform surgical procedures to treat defects of the cranial blood vessels. Advancements in catheter deployment systems have provided an alternative treatment in such cases. Some of the advantages of catheter delivery systems are that they provide methods for reduce the risk of trauma to the surrounding tissue, and they also allow for treatment of blood vessels that in the past would have been considered inoperable.

Typically, these procedures involve inserting the distal end of a delivery catheter into the vasculature of a patient and guiding it through the vasculature to a predetermined delivery site. A vascular occlusion device, such as an embolic coil, is attached to the end of a delivery member which pushes the coil through the catheter and out of the distal end of the catheter into the delivery site. Some of the problems that have been associated with these procedures relate to the accuracy of coil placement. For example, the force of the coil exiting the delivery catheter may cause the coil to over shoot the predetermined site or dislodge previously deployed coils. Also, once the coil is pushed out of the distal end of the catheter, the coil cannot be retracted and may migrate to an undesired location. Often, retrieving and repositioning the coil requires a separate procedure and has the potential to expose the patient to additional risk.

In response to the above mentioned concerns, numerous devices and release mechanisms have been developed in an attempt to provide a deployment system which allows control of the occlusion device after the device has been delivered by the catheter and to also provide a rapid release or detachment mechanism to release the device once it is in place. One such device is disclosed in Geremia et al. U.S. Pat. No. 5,108,407, which shows a fiber optic cable including a connector device mounted to the end to the optic fiber. An embolic coil is attached to the connector device by a heat releasable adhesive. Laser light is transmitted through the fiber optic cable to increase the temperature of the connector device, which melts the adhesive and releases the embolic coil. One drawback to using this type of system is the potential risk of melted adhesives contaminating the blood stream.

Another coil deployment system employs a pusher member having an embolic coil attached to the pusher member by a connector fiber which is capable of being broken by heat, as disclosed in Gandhi et al. U.S. Pat. No. 6,478,773. The pusher member of this arrangement includes an electrical resistance heating coil through which the connector fiber is passed. Electrical current is supplied to the heating coil by a power source connected to the heating coil via wires extending through an internal lumen of the pusher. The power source is activated to increase the temperature of the heating coil which breaks the connector fiber. One drawback is that connecting the resistance heating coil to the power source requires running multiple wires through the pusher member. Additionally, the electrical current traveling through the wires may create stray electromagnetic fields that have the potential to interfere with other surgical and monitoring equipment.

Yet another embolic coil positioning and delivery system is described in Saadat et al. U.S. Pat. No. 5,989,242, which discloses a catheter having a shape memory alloy connector attached to the distal end of the catheter. The connector includes a socket having a pair of spaced-apart fingers which are responsive to a change in temperature. The fingers are bent towards each other and hold a ball which is connected to an end of an embolic coil. The connector absorbs laser light transmitted through an optical cable and transforms the light into heat energy. The heat energy raises the temperature of the connector and opens the fingers, thereby releasing the embolic coil. This type of ball and socket connection is rigid and causes the catheter to be stiff, making it difficult to guide the catheter through the vasculature of the body. This patent, and all other patents and references identified herein are hereby incorporated herein by reference.

Further, the above-identified delivery systems typically require electronic equipment powered by a power source. If the electronic equipment is defective or the power source fails, the procedure may be prolonged while the equipment is repaired or replaced. Prolonging the procedure may expose the patient to additional risk.

Therefore, a need remains for a rapid release vascular occlusion deployment system or method that can function without electrical equipment or a power supply, does not develop chemical debris, is simple to manufacture, flexible and easy to guide through the vasculature of the body, provides excellent control over the occlusion device, and reduces the possibility of interference with other surgical and/or monitoring equipment.

SUMMARY OF INVENTION

The present invention embodies deployment systems and methods for accurately and rapidly deploying a vascular occlusion device at a location of concern within the vasculature of a patient. The deployment system may employ an elongated flexible delivery catheter for guiding a deployment unit to the location of concern. The deployment unit includes a delivery tube or pusher that pushes and guides the vascular occlusion device, such as an embolic coil, through the delivery catheter to the location of concern.

The pusher has a proximal end portion and a distal end portion, and a channel extending between the proximal end portion and the distal end portion. The pusher also includes an elongated member which is slidably located within the channel. The elongate member and the pusher are also able to rotate with respect to one another, i.e., the elongated member is able to rotate within the channel of the pusher, and the pusher is able to rotate around the elongated member.

The distal end portion of the elongated member is adapted for connection to an embolic device. A fracture point or breakpoint, which breaks to release the embolic device, is located on the elongated member, preferably at or near the distal end portion of the elongated member. To break the fracture point, torque is applied to one portion of the elongated member while a second portion of the elongated member is held in a substantially stationary position to resist the force of the torque applied to the first portion. Preferably, torque is applied to the proximal end portion of the elongated member, and resistance is provided at the distal end portion of the elongated member. The torque may be applied by rotating the proximal end portion of the elongated member, and the torque may be resisted at the distal end portion of the elongated member by contacting the distal end portion of the pusher with a proximal end portion of the embolic device that is attached to the distal end portion of the elongated member. In a preferred embodiment, the pusher includes a headpiece located on the distal end portion of the pusher, and the embolic device includes a headpiece located on the proximal end portion of the embolic device. The pusher headpiece and the embolic device headpiece engage each other to resist or counteract the torque applied to the proximal end portion of the elongated member.

According to one preferred method of releasing the embolic device, the elongated member and the pusher member are manipulated so that the pusher contacts the embolic device. Torque is then applied to the proximal end portion of the elongated member by rotating the proximal end portion of the elongated member. The contact between the embolic device and the pusher resists or counteracts the torque. The torque is applied until the breakpoint fractures, releasing the embolic device from the deployment unit.

Other aspects, objects and advantages of the present invention will be understood from the following description according to the preferred embodiments of the present invention, specifically including stated and unstated combinations of the various features which are described herein, relevant information concerning which is shown in the accompanying drawing.

BRIEF DESCRIPTION OF THE DRAWINGS

In describing the preferred embodiments of the present invention, reference will be made to the accompanying drawings, wherein:

FIG. 1 is an enlarged partially sectioned view of an occlusion device deployment system in accordance with a preferred embodiment of the present invention;

FIG. 2 is an exploded view of the deployment unit illustrated in FIG. 1;

FIG. 3 is an enlarged perspective view of one embodiment of the embolic device headpiece;

FIG. 4 is an enlarged perspective view of one embodiment of the pusher headpiece;

FIG. 5 is an enlarged partially sectioned view of the deployment system of FIG. 1 shown prior to deployment;

FIG. 6 is an enlarged partially sectioned view of the deployment system of FIG. 1 shown after the embolic device has exited the delivery catheter and shown with the headpieces being separated;

FIG. 7 is an enlarged partially sectioned view of the deployment system of FIG. 1 shown with the pusher engaging the embolic device after the embolic device has exited the delivery catheter; and FIG. 8 is an enlarged partially sectioned view of the deployment system of FIG. 1 shown after the embolic device has been released.

DESCRIPTION OF THE PREFERRED EMBODIMENTS

As required, detailed embodiments of the present invention are disclosed herein; however, it is to be understood that the disclosed embodiments are merely exemplary of the invention, which may be embodied in various forms. Therefore, specific details disclosed herein are not to be interpreted as limiting, but merely as a basis for the claims and as a representative basis for teaching one skilled in the art to variously employ the present invention in virtually any appropriate manner.

FIG. 1 generally illustrates a preferred embodiment of the occlusion device deployment system of the present invention. The deployment system, generally designated at 10, includes an elongated flexible delivery catheter 12 which can be inserted into the vasculature of a patient and used to guide a deployment unit, generally designated at 14, to a preselected site in a manner generally known in the art. One of ordinary skill in the art will appreciate that the delivery catheter 12 and the deployment unit 14 are much longer than illustrated in the figures.

Referring to FIGS. 1 and 2, the deployment unit 14 includes an elongated flexible pusher or delivery tube 16 having a proximal end portion 18 and a distal end portion 20. An internal channel 22 (shown in FIG. 7) extends from the proximal end portion 18 of the pusher 16 to the distal end portion 20 of the pusher. The pusher 16 may be any suitable type of pusher generally known in the art that has sufficient column strength to push an embolic device through a delivery catheter and sufficient flexibility to be guided through tortuous pathways within the vasculature of a patient. For example, the pusher may be comprised a coil wound wire, or the pusher may be a flexible polymer sheath.

An elongated member 24 is slidably disposed within the channel 22 of the pusher 16, i.e., the elongated member 24 is relatively moveable in a proximal and a distal direction with respect to the pusher 16. Additionally, the elongated member 24 and the pusher 16 are able to rotate with respect to one another, i.e., the elongated member 24 is able to rotate within the channel 22, and the pusher 16 is able to rotate around the elongated member 24.

The elongated member 24 includes a proximal end portion 26 and a distal end portion 28. The distal end portion 28 can be positioned to extend out of the distal end portion 20 of the pusher 16 so that the distal end portion 28 can be connected to an embolic device 30. The elongated member 24 also includes a breakpoint or weakened portion 32 which will break or fracture when torque is applied to either the proximal end portion 26 or the distal end portion 28 while the other end portion is held in a substantially stationary position, as will be described in more detail below. Illustratively, the breakpoint 32 is a notch, which can take the form of a partial or full notch or indent, such as a partial or full circumferential indent in the elongated member 24; however, the breakpoint 32 can be formed by any weakening of the elongated member 24 that will break or fracture upon torque being applied to the elongated member as described above, but will not prematurely break or fracture as the pusher 16 and the elongated member 24 are guided through the tortuous path of the vasculature of the patient. For example, the breakpoint 32 can also be a weakened point of attachment, a score line or a length of material that is weaker in response to torsional forces than the rest of the elongated member.

Additionally, the elongated member 24 is preferably comprised of a metallic or polymeric material which has tensile and flex properties that are greater than the torsional property required to fracture the elongated member at the breakpoint. That is, the elongated member 24 should be sufficiently strong and flexible to be guided through the tortuous path of the vasculature of the patient without prematurely fracturing the breakpoint 32.

More particularly, the elongated member (including the breakpoint) has tensile strength and flex modulus properties adequate to allow flexing, bending, pushing and pulling action during threading through a tortuous path for insertion and positioning within a vascular or intracranial system while still exhibiting a shear modulus upon torsional or twisting movement that achieves severance when desired and not prematurely. To achieve this objective, typical tensile strength of the elongated member along the breakpoint is preferably greater than the strength required when torque is applied during insertion of the elongated member. Additionally, the flex modulus of the elongated member preferably does not exceed the flex modulus of the delivery catheter and the pusher.

The embolic device 30 is preferably an embolic device assembly including an embolic element 34 and an embolic device headpiece 36. The embolic element 34 may be an embolic coil of the type which takes a substantially linear configuration for being advanced through the delivery catheter and a randomly oriented relaxed condition after it is released from the catheter. Alternatively, the embolic element 34 may be any other type of embolic element which may take on various forms and configurations, such as hydrogels, foams, bioactive coils, braids, cables and hybrid devices.

As illustrated in FIGS. 2 and 3, the embolic device headpiece 36 has a proximal end portion 38 and a distal end portion 40. The distal end portion 40 includes a joining element 42, which is illustratively shown as a cylindrical projection, for connecting the embolic element 34 to the headpiece 36. The joining element 42 and the embolic element 34 may be attached to each other by weld, solder, adhesive or any other suitable attachment method. The headpiece 36 can include an opening 44 for accepting the distal end portion 28 of the elongated member 24 for attachment. The elongated member 24 and headpiece 36 may also be attached by weld, solder, adhesive or any other suitable method of attachment. Illustratively, the embolic device 30 is comprised of the headpiece 36 and the embolic element 34 which are separate components that are secured together; however, it will be understood by one of ordinary skill in the art that the embolic element and the headpiece can be of unitary construction to form the embolic device 30.

The proximal end portion 38 of the headpiece 36 includes an arrangement for positively engaging the pusher, typically a headpiece thereof. By such an engagement, the embolic device headpiece and the pusher headpiece will not rotate circumferentially in a manner independent of each other.

A preferred engagement arrangement in this regard includes an engagement member 41 of headpiece 36 which engages a corresponding engagement member 43 of a pusher headpiece 45. The illustrated respective engagement members 41, 43 each embody a partial circumferential projection in the axial direction, and such projections contact one other and can be complementary with each other. When desired, the projections combine to form a circumference with engagement surfaces that contact one another. In a preferred embodiment, the projections combine to form a shape having an axial or central axis, such as a cylinder.

As shown in the illustrated embodiment, engagement surfaces 48, 48a and 50, 50a can be along an axis aligned parallel to the central axis of the cylinder formed by the mated engagement members 41, 43. The engaging surfaces also need not be parallel to the central axis but can be at an acute angle to the central axis of the cylinder. Also, each engagement surface can be along a common plane that is parallel to the central axis of the cylinder. Alternatively, the engagement surfaces of each headpiece can be along separate planes that do not intersect. For example, each engagement surface could be along a different plane wherein each plane is separated by a distance. This would also include engagement surfaces of the same headpiece that are beveled in the same direction at the same angle.

In yet another alternative, the engagement surfaces can be along separate planes that intersect. For example, in the illustrated embodiment the engagement surfaces 48, 48a of a headpiece 36 could be beveled inwardly toward each other, or the engagement surfaces could be beveled outwardly away from each other. The engagement surfaces typically can be planar, or flat, but can have a curved configuration or component. For example, the engagement surfaces could have a tongue and groove mating configuration wherein an engagement surface of one headpiece could have a tongue, and the corresponding engagement surface of the other headpiece could have a corresponding groove which mates with the tongue when the engagement members are engaged.

The engagement surfaces interact with each other to provide interference with independent circumferential movement of the headpieces while allowing independent movement of the embolic device 30 and the pusher 16 axially when it is desired to deploy the embolic device. The illustrated engagement member 41 of the embolic device headpiece 36 is a semi-circular projection 46 which includes engagement surfaces that are flats 48, 48a located on either side or edge of the projection 46. The flats 48, 48a in this illustrated embodiment engage corresponding engagement surfaces, such as flats 50, 50a, located on a semi-circular projection 52 of engagement member 43 of the pusher headpiece 45 shown in FIG. 4.

As will be explained in more detail below, the arrangement for positively engaging the respective headpieces functions as follows according to the illustrated preferred embodiment. The pusher headpiece 45 and the embolic device headpiece 36 engage each other to resist or counteract torque applied to the proximal end portion 26 of the elongated member 24. Alternatively, the engagement of the pusher headpiece 45 and the embolic device headpiece 36 can be employed to apply torque to the distal end portion 28 of the elongated member 24.

As shown in FIG. 4, the illustrated pusher headpiece 45 also includes a proximal end portion 56. The proximal end portion 56 includes a joining element 58, which is illustratively shown as a tubular projection, for joining the headpiece 45 to the pusher 16. The distal end portion 20 of the pusher 16 engages, such as by fitting over, the joining member 58. The joining member 58 and the pusher 16 can be connected by weld, solder, adhesive or any other suitable method known in the art. The headpiece 45 also includes a passageway 60 which allows the elongated member 24 to extend therethrough and project from the distal end portion 20 of the pusher 16.

In operation as a vascular occlusion deployment system, referring to FIGS. 5-8, the delivery catheter 12 can be inserted into the vasculature system of a patient, and the distal end portion 62 of the catheter 12 can be positioned at a preselected location within a blood vessel, typically in conjunction with other devices and professional procedures as generally known in the art. The delivery unit 14 is inserted into a proximal end portion 64 the catheter 12, and preferably the delivery unit 14 is advanced through the delivery catheter 12 until the embolic device 30 reaches the distal end portion 62 of the delivery catheter 12. If desired, the pusher headpiece 45 and the embolic device headpiece 36 can be engaged to increase column strength during the advancement of the pusher 16.

Once the embolic device 30 reaches the distal end portion 62 of the delivery catheter 12, the embolic device 30 may be moved out of the distal end portion 62 of the delivery catheter 12 in one of several ways. The delivery catheter 12 may be moved in a retrograde manner as indicated by arrow A. Alternatively, the pusher 16 may be advanced as indicated by arrow B. As a further alternative, the embolic device 30 may be advanced out of the delivery catheter 12 by advancing the elongated member 24 in a distal direction. Yet another alternative can be to employ any of the above methods in conjunction with one another.

The embolic device 30 preferably includes a radiopaque marker so that the position of the embolic device 30 can be monitored by fluoroscopy. Referring to FIG. 6, after the embolic device 30 has exited the delivery catheter 12, if required, the elongated member 24 can be manipulated to more precisely place the embolic device 30 at the desired location. If it is determined that the embolic device 30 is in the wrong position and/or a different embolic device is required, the pusher 16 and the elongated member 24 can be retracted to move the embolic device 30 back into the delivery catheter 12. Once in the delivery catheter 12, the embolic device 30 can be repositioned or completely removed from the patient.

After it has been determined that the embolic device 30 is at the desired location within the patient, and if not already in engagement, the headpieces are so engaged. Typically, as illustrated in FIG. 7, the pusher headpiece 45 is engaged with the embolic device headpiece 36 so that the corresponding engagement surfaces, such as flats 48, 48a and 50, 50a, engage each other. Engagement of the headpieces 36 and 45 can be accomplished as needed by advancing the pusher 16 in a distal direction as indicated by arrow C. It is also contemplated that in certain situations, it may be advantageous to engage the headpieces 36 and 45 by moving the elongated member 24 in a proximal direction as indicated by arrow D.

After the headpieces 36 and 45 have been engaged according to this illustrated embodiment, the embolic device 30 can be released by fracturing the breakpoint 32 on the elongated member 24. Preferably, the breakpoint 32 is fractured by rotating the elongated member 24 circumferentially, as illustrated by arrow E (or in the opposite circumferential direction as desired), to apply torque to the proximal end portion 26 of the elongated member 24. As torque is applied to the proximal end portion 26 of the elongated member 24, torque is resisted by the engagement along the headpieces, such as between the flats 48, 48a and 50, 50a respectively of the respective headpieces 36 and 45. The engagement of the headpieces limits or reduces rotational movement of the distal end portion 28 of the elongated member 24, causing the breakpoint 32 to fracture. In keeping with the invention, the engagement of the headpieces maintains the distal end portion of the elongated member in a substantially stationary position as torque is applied to the elongated member. Additionally, the engagement between the headpieces 36 and 45 limits or reduces the undesired rotational movement of the embolic device 30. When the pusher 16 is comprised of a coiled wire, it is preferable to rotate the pusher 16 in a direction opposite the wind of the coil to avoid buckling or kinking the pusher.

It is also contemplated that there may be situations where it would be advantageous to fracture the breakpoint 32 by applying torque to the distal end portion 28 of the elongated member 24 by rotating the pusher 16 while maintaining the proximal end portion 26 of the elongated member 24 in a substantially stationary position. By this approach, the rotational movement of the pusher 16 is translated therealong, through the headpieces, to the embolic device, and to the length of the elongated member secured to the embolic device. At the same time, the rest of the elongated member is held in a substantially stationary position that resists rotation, resulting in the desired fracture of the breakpoint.

As illustrated in FIG. 8, after the breakpoint 32 fractures, the embolic device 30 can be released for deployment at a desired location within the patient such as within or at an aneurysm. The pusher 16 may now be retracted through the delivery catheter 12 and removed from the patient.

It will be understood that the embodiments of the present invention which have been described are illustrative of some of the applications of the principles of the present invention. Numerous modifications may be made by those skilled in the art without departing from the true spirit and scope of the invention, including those combinations of features that are individually disclosed or claimed herein.

The invention claimed is:

1. A vascular occlusion device and deployment system, comprising;
   a pusher member that is a tube having an elongated internal channel, a proximal end portion and a distal end portion;
   an elongated member positioned within said pusher member and relatively rotatable with respect to said internal channel of the pusher member, said elongated member having a proximal end portion and a distal end portion;
   an embolic device, said embolic device being connected to the distal end portion of said elongated member, the embolic device having a headpiece that includes an engagement member;
   a breakpoint located on the elongated member at or near the distal end portion of the elongated member, said breakpoint comprising a notch in the elongated member;
   the distal end portion of the pusher member has a headpiece that includes an engagement member that engages the engagement member of the embolic device, said embolic device and pusher member engagement members each having a proximal end and a distal end;
   the engagement member of the pusher member and the engagement member of the embolic device mate to form a shape having an axial axis;
   the engagement member of the pusher member includes an engagement surface that is axially oriented and extends to the distal end of its said engagement member and in a direction that is generally parallel to said axial axis;
   the engagement member of the embolic device includes an engagement surface that is axially oriented and extends to the proximal end of its said engagement member and in a direction that is generally parallel to said axial axis;
   the engagement surface of the engagement member of the pusher member opposes and contacts the engagement surface of the engagement member of the embolic device when said engagement members contact one another to thereby limit relative rotational movement between the pusher member and the embolic device;
   the breakpoint notch breaks when the pusher member is engaged with the embolic device and mechanical torque is applied through the pusher member by rotation of the proximal end portion of the elongated member, the torque being transmitted to the breakpoint while rotation of the embolic device and the distal end portion of the elongated member is prevented; and
   the embolic device, its headpiece and the distal end portion of the elongated member are detached from the pusher member and from the proximal end portion of the elongated member when the breakpoint breaks, at which time the respective engagement surfaces of the pusher member and embolic device freely slide in opposite directions along a common longitudinal path and without radial displacement, the longitudinal path being substantially parallel to said axial axis.

2. The occlusion device and deployment system of claim 1, wherein the engagement surface of the engagement member of the pusher member and the opposing engagement surface of the engagement member of the embolic device are substantially planar.

* * * * *